(12) United States Patent
Hoo Fatt et al.

(10) Patent No.: US 7,320,242 B2
(45) Date of Patent: Jan. 22, 2008

(54) TENSILE IMPACT APPARATUS

(75) Inventors: Michelle S. Hoo Fatt, Akron, OH (US); Ibrahim Bekar, Stow, OH (US); Joseph Padoyan, Akron, OH (US)

(73) Assignee: The University of Akron, Akron, OH (US)

( * ) Notice: Subject to any disclaimer, the term of this patent is extended or adjusted under 35 U.S.C. 154(b) by 539 days.

(21) Appl. No.: 10/387,095

(22) Filed: Mar. 12, 2003

(65) Prior Publication Data
US 2004/0040369 A1 Mar. 4, 2004

Related U.S. Application Data

(60) Provisional application No. 60/363,707, filed on Mar. 12, 2002.

(51) Int. Cl.
*G01M 7/00* (2006.01)

(52) U.S. Cl. ..................................... 73/12.14
(58) Field of Classification Search ..... 73/12.01–12.14
See application file for complete search history.

(56) References Cited

U.S. PATENT DOCUMENTS

| | | | | |
|---|---|---|---|---|
| 3,224,259 A | * | 12/1965 | De Nicola ................ | 73/859 |
| 3,335,603 A | * | 8/1967 | Gram .................... | 73/857 |
| 3,927,558 A | * | 12/1975 | Philippe et al. .......... | 73/816 |
| 4,041,806 A | * | 8/1977 | Klar .................... | 73/159 |
| 4,210,789 A | * | 7/1980 | Ushiku et al. ........ | 200/61.45 R |
| 4,212,192 A | * | 7/1980 | Taylor .................... | 73/45.5 |
| 4,302,106 A | * | 11/1981 | Taylor .................... | 356/241.1 |
| 4,432,520 A | * | 2/1984 | Simon .................... | 248/56 |
| 4,537,080 A | * | 8/1985 | Christiansen ............ | 73/857 |
| 5,156,053 A | * | 10/1992 | Shiraishi et al. ........ | 73/849 |
| 5,770,791 A | | 6/1998 | Manahan, Sr. ........ | 73/12.01 |
| 6,044,713 A | | 4/2000 | Bassily .................. | 73/849 |
| 6,721,667 B2 | * | 4/2004 | Banes et al. ............ | 702/41 |
| 6,769,287 B2 | * | 8/2004 | Stewart et al. ........ | 73/12.01 |
| 2002/0019187 A1 | * | 2/2002 | Carroll et al. ........ | 442/394 |

OTHER PUBLICATIONS

"Deformation and Fracture of Rubber Under Tensile Impact Loading", I. Bekar et al., presented Apr. 24-25, 2001.
B.A. Dogadkin and D.M. Sandromirski, "Effect of Temperature and the Rate of Stretching on the Tensile Strength of Vulcanites", Rubber Chemistry and Technology, vol. 25, 1952, pp. 50-52.
D.S. Villars, "Ultra Speed Tensile of Rubber and Synthetic Elastomers", J. Appl. Phys., vol. 21, 1950, pp. 565-573.
H.W. Greensmith, "Rupture of Rubber: Effect of Rate of Extension in Tensile Tests", Journal of Applied Polymer Science, vol. 3, No. 8, 1960, pp. 175-182.

(Continued)

*Primary Examiner*—Max Noori
(74) *Attorney, Agent, or Firm*—Roetzel & Andress, LPA; George W. Moxon, II

(57) ABSTRACT

The present invention generally relates to a tensile impact apparatus that is designed to give dynamic stress-strain curves and fracture characteristics for a rubber specimen undergoing tensile impact loading. More particularly, this invention relates to a tensile impact apparatus that is capable of achieving strains of up to fracture. The apparatus is also capable of visually recording fracture phenomena.

6 Claims, 9 Drawing Sheets

OTHER PUBLICATIONS

M.L. Williams, R.F. Landel and J.D. Ferry, "The Temperature Dependence of Relaxation Mechanisms in Amorphous Polymers and Other Glass-Forming Liquids", J. Am. Chem. Soc., vol. 77, 1955, pp. 3701-3707.

T.L. Smith, "Dependence of the Ultimate Properties of GR-S Rubber on Strain Rate and Temperature", Journal of Polymer Science, vol. 32, 1958, pp. 99-113.

J. S. Bergstrom and M. C. Boyce, "Constitutive Modeling of the Large Strain Time-Dependent Behavior of Elastomers", J. Mec. Phys. Solids, vol. 46, No. 5, 1998, pp. 931-954.

L. M. Yang, V.P.W. Shim, C.T. Lim, "A Visco-Hyperelastic Approach to Modeling the Constitutive Behavior of Rubber", International Journal of Impact Engineering, vol. 24, 2000, pp. 545-560.

\* cited by examiner

Long range scale    Local scale

TENSILE IMPACT APPARATUS

This application gains priority from U.S. Provisional Application No. 60/363,707, filed on Mar. 12, 2002.

BACKGROUND OF THE INVENTION

The present invention relates to a tensile impact apparatus that is designed to give dynamic stress-strain curves of uniaxial strip specimens and force-extension curves for notched specimens and further provides for visual observation and study of fracture characteristics for a rubber specimen undergoing tensile impact loading.

Various types of hi-speed tensile impact test equipment are currently available, including open-and closed-loop hydraulic systems; pneumatic systems; pneumatically actuated, hydraulically damped systems; resonant beam systems; and pendulum impact systems. Other types of impact test equipment, such as those employing fly wheels, smokeless powder-driven actuators, and dual-opposing actuators are available for special test applications; however, these types of test equipment are typically custom made for such applications, and the demand for such equipment is therefore quite limited. Furthermore, they only provide tensile strength and fracture strain and do not give dynamic stress-strain curves at very high rates. While present-day apparatus, such as the tensile Split Hopkinson Pressure Bar and expansion ring tests, can provide dynamic stress-strain curves at very high rates, they are not designed to monitor how the specimen fractures. In distinction, the tensile impact apparatus described herein gives both dynamic stiffness and strength characteristics of rubber and is capable of monitoring specimen fracture.

Until recently, there has been very little need for understanding the tensile impact response of an elastomer (rubber-like) material at large strains and high strain rates. Typical elastomeric structures, such as vibration isolators, shock pads and base isolation bearings, carry loads in compression and/or shear and operate in regimes where the engineering strains are below 100%. However, as uses for polymeric materials become more widespread and diverse, the ability to characterize tensile behavior at large strains and high strain rates will be very useful. For example, the Air Force Research Laboratory (AFRL) at Tyndall Air Force Base (AFB) discovered that polyurethane elastomer coatings on concrete blocks, reinforced concrete, and trailer walls could offer significant protection for occupants when the walls were subjected to air blast or explosive loading. T. R. Anderl, "Space-age coating protecting against terrorism," Air Force Research Laboratory Materials and Manufacturing Directorate, 10 Feb. 2003. The hyper-viscoelastic behavior of the polyurethane rubber allowed the coated wall to flex and absorb blast energy. The elastomer itself also provided a nesting zone for blast fragments and prevented harmful projectiles from entering buildings. In order for the Air Force to understand the blast protection effectiveness of elastomer coatings, it is necessary or at least helpful to characterize tensile behavior of elastomers at large strains and high strain rates ($10$-$10^3$ $s^{-1}$).

As another example, rubber may break under very high strain rates in tire applications. For example, a faulty tire on a car traveling at 55 mph (89 km/h) may suddenly break at a shear strain rate of 404 $s^{-1}$ when it hits a bump in the road. Unfortunately, currently accepted test methods for determining the mechanical properties of rubber in the tire industry cannot provide adequate data to predict this type of failure. Creep and relaxation tests determine rubber properties under quasi-static loading, while vibration and rebound tests determine loss and storage modulus for vibratory loads. The vibration and rebound tests may be capable of reaching high rates or frequencies but are limited by low strains (well below the tensile fracture strain of rubber).

Dynamic material properties for elastomers are often specified for structural response in the frequency rather than the time domain. Vibration experiments are used to find complex modulus in the frequency domain and this data is often used to design shock absorbers and base isolation bearings. J. M. Kelly, "Earthquake Resistant Design with Rubber," Springer-Verlag, London, 1997. However, the concept of a complex modulus is based on linear viscoelastic material behavior, i.e., material for which stress is directly proportional to strain and strain rate. Frequency domain material properties are therefore limited to applications where strains are small and stress is approximately linear with strain and the strain rate. Frequency domain material properties become irrelevant if the material exhibits nonlinear elastic behavior or is subjected to large strains. Under tension, elastomers are not only nonlinear elastic but also hyperelastic, i.e., they can stretch 300-500% before breaking. Clearly, new dynamic material properties are needed to characterize elastomeric structures undergoing high strain rates and nonlinear, hyperelastic behavior.

Thus, there exist a need to develop a tensile impact apparatus that is designed to give dynamic stress-strain curves of a rubber specimen undergoing tensile impact loading. Particularly, there is a need for an apparatus that is capable of achieving strains sufficient to fracture virtually any elastomer sample. The data provided by the tensile impact apparatus would enable one to predict tensile fracture of rubber components under shock or impact loads.

SUMMARY OF THE INVENTION

The present invention provides a tensile impact apparatus including a slider bar having an impact surface and capable of sliding on a support member; a first guided base retained on a support rail and capable of linear movement thereon, the first guided base communicating with a first grip through a first load cell; a second guided base retained on a support rail and capable of linear movement thereon, the second guided base communicating with a second grip through a second load cell, wherein the first and second grips are substantially aligned for linear movement with their respective first and second guided bases, toward or away from each other, and further being adapted for gripping opposed ends of a rubber sample; a first cable connected between the slider bar and the first guided base; a second cable connected between the slider bar and the first guided base; a first displacement transducer associated with the first guided base; a second displacement transducer associated with the second guided base; and a pendulum adapted for striking the slider bar such that, when the pendulum strikes the slider bar, the slider bar slides on its associated support member and pulls the first and second cables such that the first and second guided bases are substantially simultaneously moved away from each other by the pulling force of their respective first and second cables, and the first and second grips are also substantially simultaneously moved away from each other due to their respective communication with their first and second bases through the first and second load cells.

This invention also provides a process for testing a rubber sample under tensile impact loading comprising the steps of securing a rubber sample at opposed ends thereof, and moving the opposed ends away from each other substantially simultaneously and at substantially identical velocities such that the middle of the rubber sample remains substantially stationary, while the movement of the opposed ends stretches the rubber sample at impact rates. As used herein "impact rates" is to be understood to mean strain rates of at least 10 s$^{-1}$, although, notably, strain rates of at least 100 s$^{-1}$ are more particularly desired in the present invention, and strain rates of 1000 s$^{-1}$ and larger may be achieved through this invention.

Thus, a pendulum is employed to strike a slider bar that serves to stretch a rubber sample. Typically, the sample is stretched until failure, in order to determine the impact fracture behavior of the sample. The rubber sample is stretched by the movement of both ends of the sample away from each other, thereby creating greater stains and strain rates. Strains of over 400% and strain rates of 1,000 s$^{-1}$ have been achieved with this tensile impact apparatus, and larger strains and higher strain rates are possible and practical. Indeed, it is believed that any strain sufficient to fracture a given elastomer sample can be achieved under impact loads with this apparatus. Additionally, because both ends of the sample are dynamically pulled apart during testing, the mid-section of the sample, which in some experiments may be "notched" or "cracked," as it is known in the art, remains in a fixed position such that it is possible to observe fracture phenomena with a stationary camera focused on the mid-section of the sample. Optical observation of the fracture phenomena may yield useful information relating to crack tip blunting or the crack tip opening angle and displacement as the crack propagates.

PREFERRED EMBODIMENT FOR CARRYING OUT THE INVENTION

In order to simulate high strain rate range behavior, the tensile impact apparatus of this invention is based upon a Charpy apparatus designed for metals, rather than one designed for polymers and elastomers, because the pendulum height and weight for the Charpy apparatus used for polymers is too small to provide the necessary high impact velocities. The weight of the pendulum, which provides inertial forces, is not sufficient to achieve constant deformation rates throughout the experiment.

The tensile impact apparatus is designed to give dynamic stress-strain curves of an elastomer dumbbell (strip) specimen undergoing tensile impact loading until failure. The apparatus is able to achieve strains sufficient to fracture, and strain rates in the range of 10-1,000s$^{-1}$ and even greater are possible.

Figure 1A:
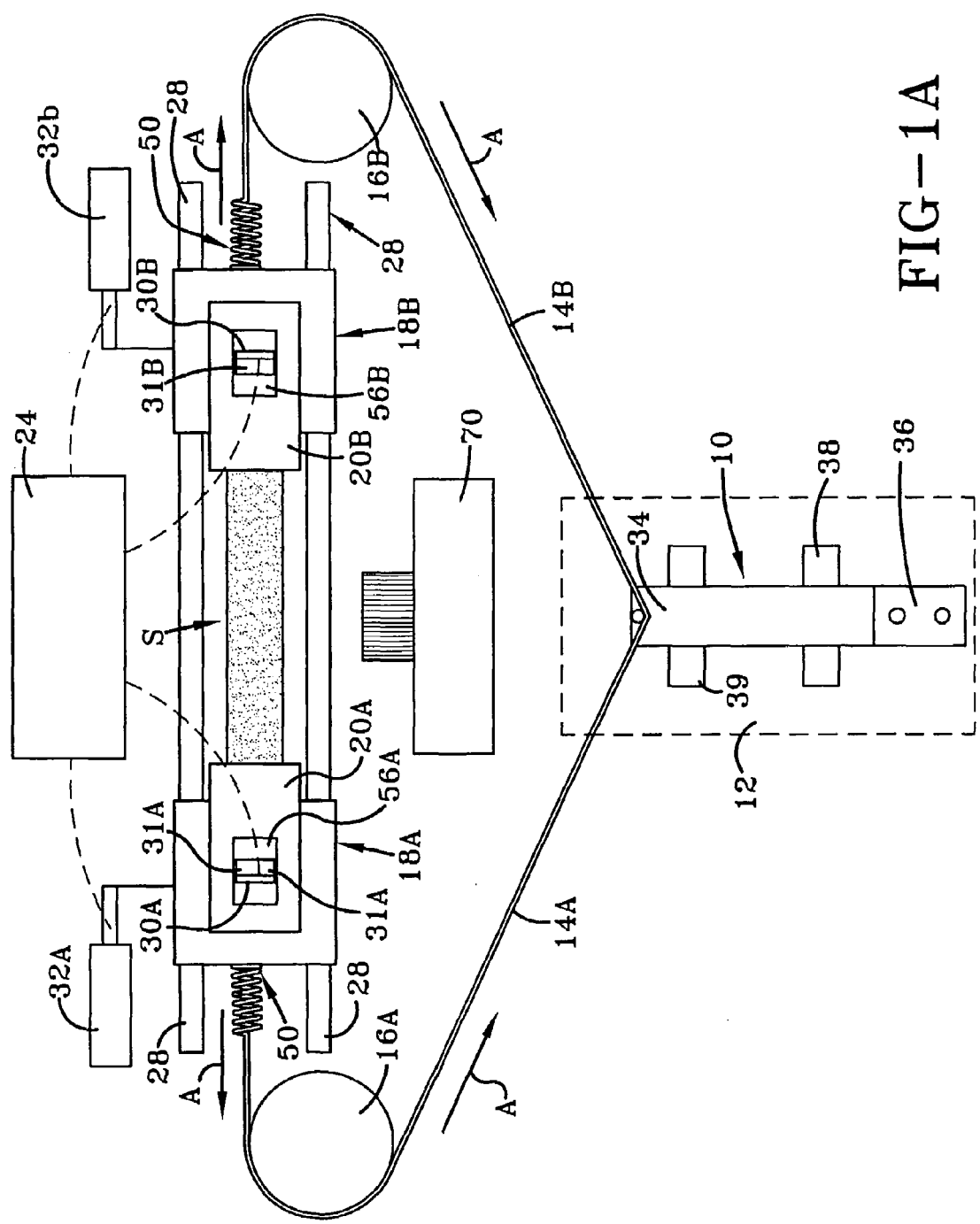
FIGS. 1A (top plan view) and 1B (side view) together depict the tensile impact apparatus of this invention, the Charpy impact machine of FIG. 1B being generally represented in FIG. 1A by a dashed box so as to allow for viewing of the slider bar.
Figure 1B:
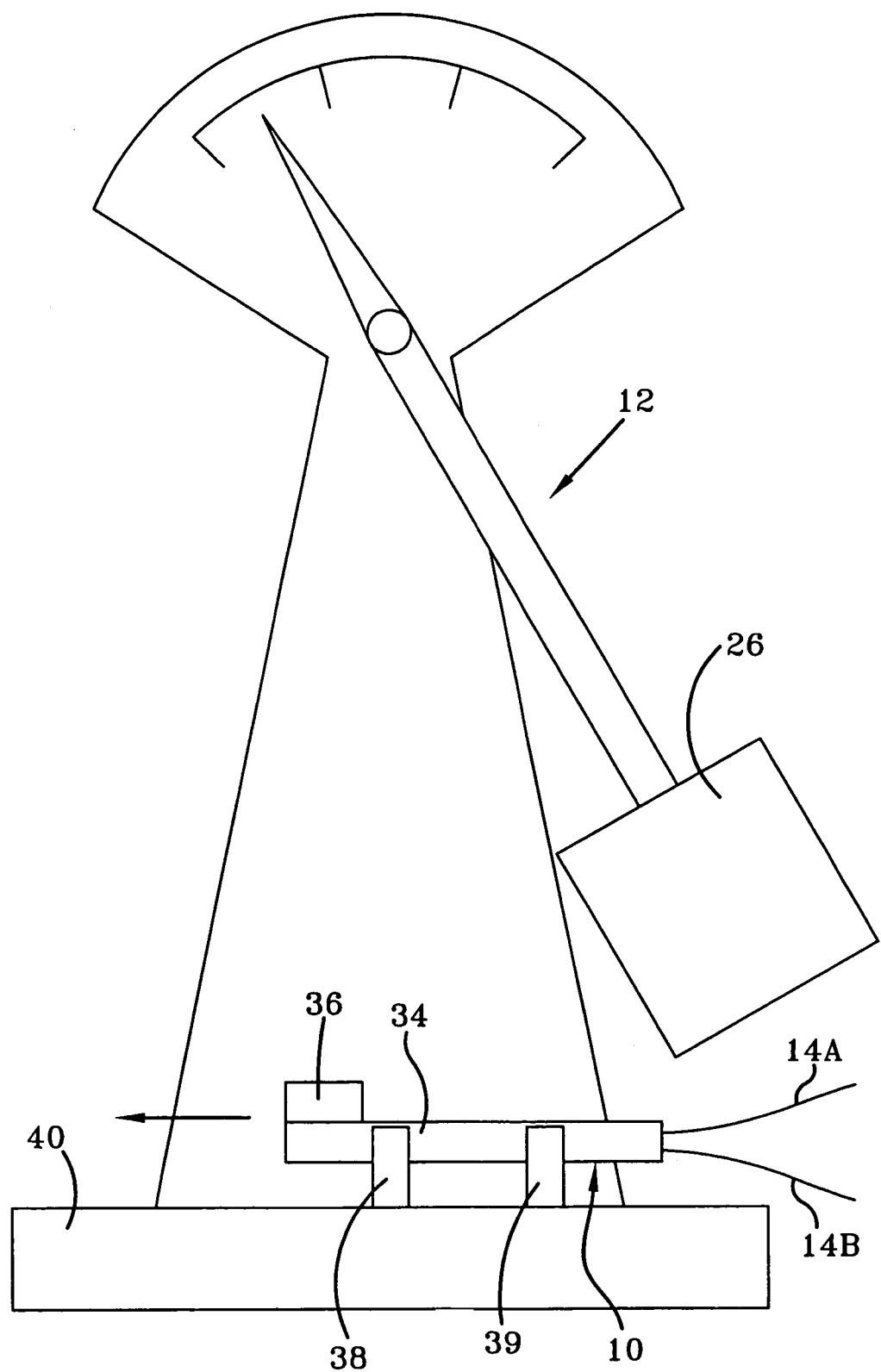

A schematic of the tensile impact apparatus is provided in FIGS. 1A and 1B. The four basic components of the testing apparatus include (1) a slider bar 10 and associated Charpy impact machine 12, (2) a cable and pulley system, including cables 14A, 14B with associated pulleys 16A and 16B (3) guided bases 18A, 18B and associated grips 20A, 20B, and (4) a signal conditioner and data acquisition system 24.

Pendulum 26 of Charpy impact machine 12 is made to strike slider bar 10, which pulls cables 14A, 14B that are attached thereto. Cables 14A, 14B are directed around pulleys 16A, 16B, which are fixed to a rigidly supported test fixture (not shown), and the tensile impact force transferred to cables 14A, 14B via pendulum 26 and slider bar 10 is transferred to rubber specimens S by pulling guided bases 18A, 18B in the direction of arrows A. Guided bases 18A, 18B slide freely on steel rails 28, and will be better appreciated with reference to FIG. 5 and its associated disclosure. Generally, guided bases 18A, 18B include grips 20A, 20B, which hold the opposite ends of rubber specimen S; load cells 30A, 30B, which are mounted on plates 31A, 31B and communicate between guided bases 18A, 18B and grips 20A, 20B to measure the load; and displacement transducers 32A, 32B, which measure the displacement of opposite ends of specimen S, particularly, the displacement of guided bases 18A, 18B. These load and displacement signals are sent to signal conditioner and data acquisition system 24 for data processing, the signal transmission being represented in FIG. 1A by the dashed lines to system 24. From system 24, the data is analyzed, by computer or microprocessor, in conventional ways.

In use of apparatus 10, dynamic load cells 30A, 30B are subject to vibrate and thus produce "noisy" data, and a signal conditioner is thus employed. If the displacement transducers produce voltages too low for recordation and/or analysis, an amplifier should also be employed to transmit the displacement signals to data acquisition system 24.

Figure 2:
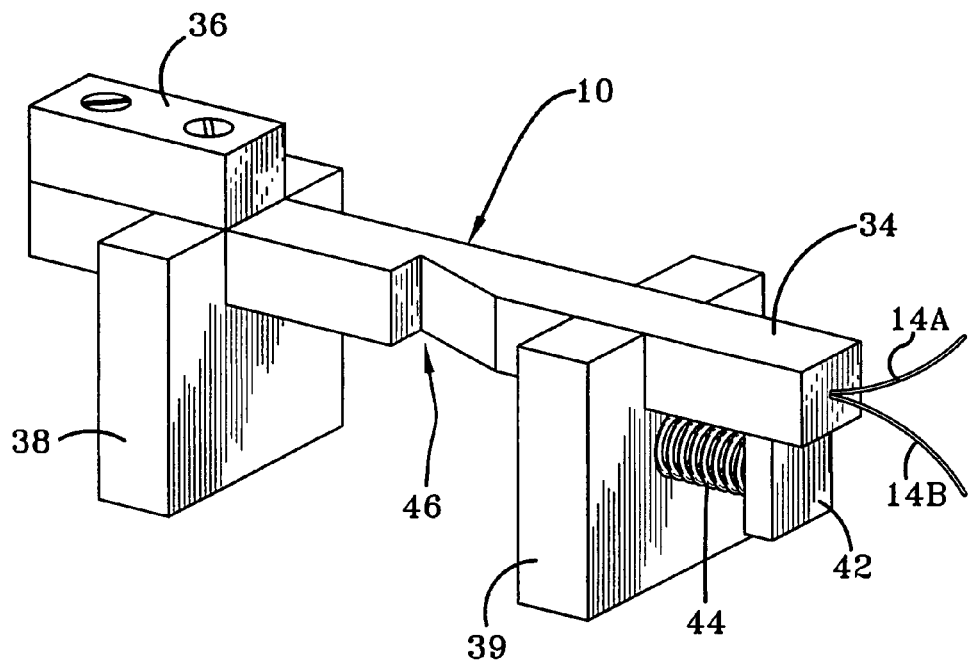
FIG. 2 provides a detailed view of the slider bar portion of the tensile impact apparatus.
Figure 3:
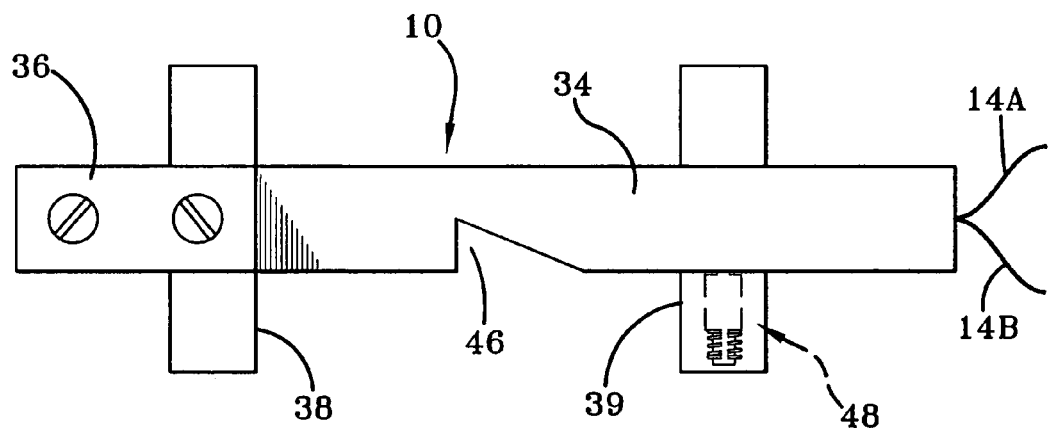
FIG. 3 is a top view of the slider bar and associated supports.

Referring additionally to FIGS. 2 and 3, it can be seen that slider bar 10 is designed to pull copper cables 14A, 14B upon impact by pendulum 26. Thus, circular motion of pendulum 26 is converted to linear motion, by striking one end of slider bar 10 with pendulum 26. Slider bar 10 is a rectangular, preferably brass, bar 34 with a rectangular, preferably steel, block 36 mounted on one side thereof. Bar 34 slides on two grooved, preferably aluminum, supports 38, 39 that are mounted on the base 40 of Charpy impact machine 12. Friction between bar 34 and supports 38, 39 can be minimized with a good lubricant. Additionally, providing a brass bar 34 and aluminum supports 38, 39 provides a good friction interface for the apparatus. At the opposite side of slider bar 10, plate 42 is mounted to restrict the excessive movement of slider bar 10. When pendulum 26 strikes block 36, slider bar 10 moves and causes plate 42 to compress coil spring 44 that connects between the plate 42 and grooved support 39. As plate 42 rebounds off spring 44, notch 46 on one side of bar 34 moves toward grooved support 39, which contains a spring-loaded pin 48, which is shown in phantom in FIG. 3 due to its hidden nature. Spring-loaded pin 48 slips into notch 46, and prevents slider bar 10 from moving backwards on the rebound.

The speed imparted to grips 20A, 20B upon impact with pendulum 26 can be adjusted by varying one or more of the drop height and mass of pendulum 26. In the embodiment currently reduced to practice, the maximum drop height for pendulum 26 is 60 inches, and pendulum 26 weighs about 30 lbs., thus providing adequate inertia and tension in the cable to break the specimens tested herein. The force of impact on block 36 of slider bar 10 will affect grip velocity, which will also be affected by the specimen itself, particularly, its resistance to the force imparted. Again, it is desired to design the apparatus to fracture a desired rubber/elastomer sample, and, based upon the forgoing, those of ordinary skill in the art could, without undue experimentation, select a drop height and weight for pendulum 26 and a stroke length for slider bar 10 that would be sufficient to fracture a given sample. The stroke length can be adjusted by simply repositioning slider bar 10 at the beginning of a test. Notably, the total grip displacement is twice as much as the stroke length of slider bar 10, because the motion of slider bar 10 is transferred equally to the two grips 20A, 20B. Likewise, the grip velocity is twice that of the slider bar velocity.

Grips 20A, 20B are designed to be unconstrained, i.e., they move freely upon tensile impact loading. The only contact between grips 20A, 20B and guided bases 18A, 18B is through load cells 30A, 30B, which are mounted on plates 31A, 31B that are bolted to guided bases 18A, 18B. Cables 14A, 14B, attached to slider bar 10, pull guided bases 18A, 18B, which slide freely along parallel rails 28, which are preferably made of steel for purposes of reducing friction.

Figure 4:
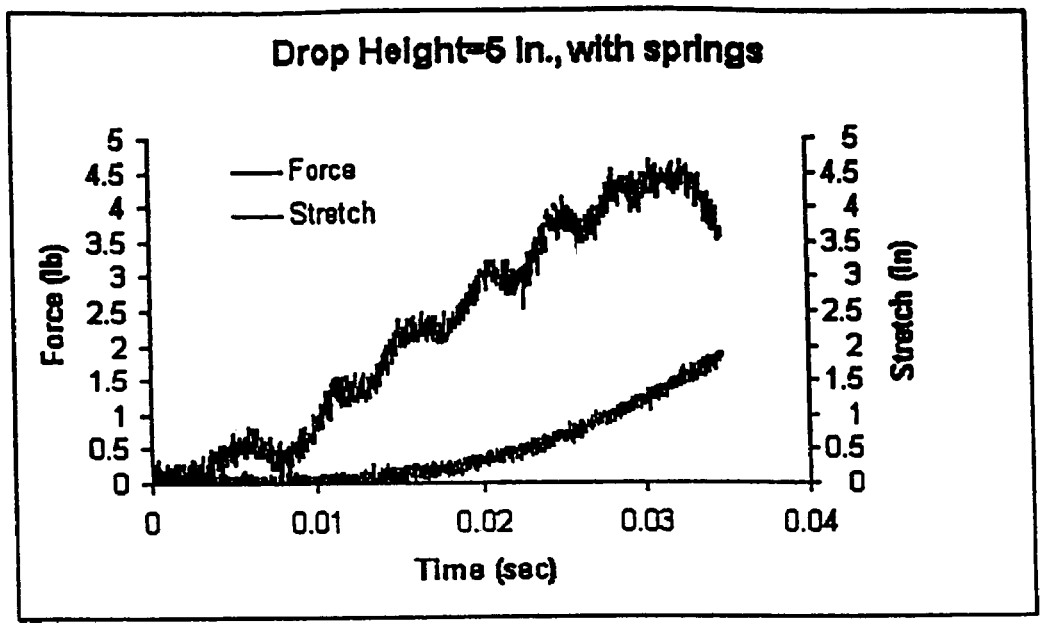
FIG. 4 provides graphs of tensile force versus time for comparison of the tensile load applied to the guided bases when their associated cables are attached (a) with springs and (b) without springs.
Figure 4:
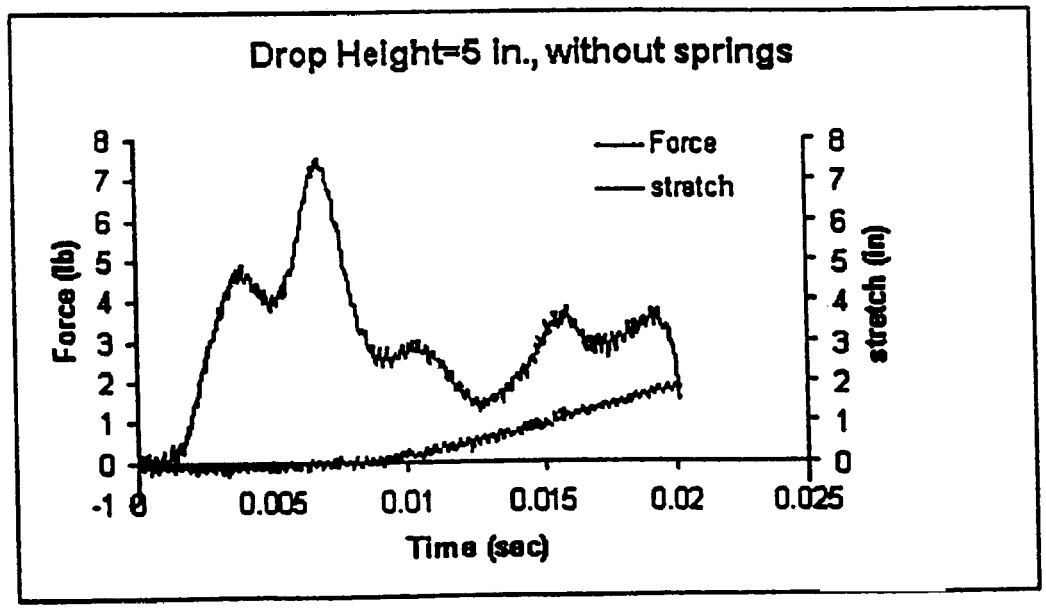

Cables 14A, 14B transfer the motion of slider bar 10 to the opposed ends of rubber specimen S. Copper cables are preferably used because copper is flexible, lightweight and does not kink, although the recitation of copper cables is to be non-limiting, and other cable materials might be found to be adequate. Each cable 14A, 14B is connected to slider bar 10 at one end, directed around an associated pulley 16A, 16B, and attached to a respective guided base 18A, 18B at its opposite end. In a particularly preferred embodiment, each cable 14A, 14B is connected to its respective guided base 18A, 18B by coil spring 50, which serves to smooth out the applied tensile load, as can be clearly seen in the graphs of FIG. 4.

The two guided bases 18A, 18B are thus displaced by the impact of pendulum 26 on slider bar 10, and guided bases 18A, 18B, through plates 31A, 31B and load cells 30A, 30B, transfer the load and displacement to grips 20A, 20B and, thus, to opposite ends of rubber specimen S. Guided bases 18A, 18B are better understood with reference to FIG. 5, wherein guided base 18A is depicted, it being understood that guided base 18B is identical except for its orientation in apparatus 10. Therein, it is seen that grip 20A, is made by clamping two plates 52A, 53A with screws 54A. The two plates 52A, 53A together provide a rectangular slot 56A so that load cell 30A and associated plate 31A can fit therein. Plate 31A is fixed to support plate 58A (means of affixation not visible, although any appropriate means might be employed), which is fixed on top of guides 60A, 62A with screws 59A. Guides 60A, 62A include bores 64A, 66A through which run rails 28. The surface of bores 64A, 66A is preferable coated with brass to reduce friction between guided base 18A and steel rails 28. Grip 20A holds its respective end of rubber specimen S by placing an end of rubber specimen S between the two plates 52A, 53A, when screws 54A are sufficiently loose, and thereafter tightening screws 54A to clamp specimen S in between the two plates 52A, 53A.

Figure 5:
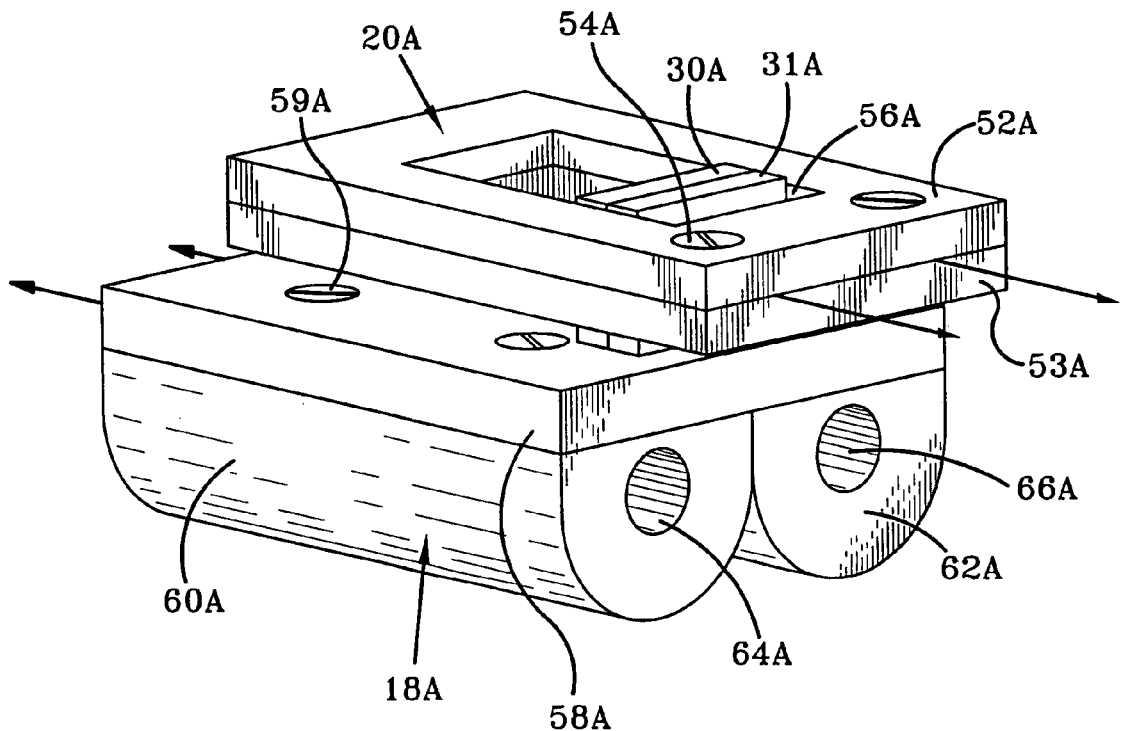
FIG. 5 is a detailed perspective view of a guided base element of the tensile impact apparatus of this invention.

Guided bases 18A, 18B, as understood from FIG. 5, are specifically designed to communicate with the grips 20A, 20B that hold specimen S. More particularly, load cells 30A, 30B are fixed to respective guided bases 18A, 18B and extend upwardly into respective slotted grips 20A, 20B on plates 31A, 31B. Upon movement of guided bases 18A, 18B via cables 14A, 14B, load cells 30A, 30B hit the backside of the slots 56A, 56B within grips 20A, 20B and, thus, grips 20A, 20B pull on specimen S. Guided bases 18A, 18B slide freely on two parallel steel rails 28, while grips 20A, 20B are maintained in position by load cells 30A, 30B. Grips 20A, 20B are keyed on to guided bases 18A, 18B by load cells 30A, 30B. By having grips 20A, 20B contact load cells 30A, 30B, the tensile force is measured by load cells 30A, 30B as a compressive force on the backside of slots 56A, 56B within grips 20A, 20B. Linear variable differential transformers (LVDT displacement transducers) are also attached to guided bases 18A, 18B to measure the distance of grip separation. The range of the displacement transducers used in the preferred embodiment is ±150 mm, but there is no limit to the range that might be employed, it being understood that certain types of rubber samples might stretch more or less, and require greater or lesser ranges.

Load cells 30A, 30B are quartz force sensors on piezoelectric load cells. Piezoelectric load cells are recommended for dynamic force applications, because of their fast response and the ability to measure impact forces. The range of the load cells should be chosen according to the rubber/elastomer under study, with higher tensile strength elastomers needing higher ranges.

The time of an experiment, from the impact of the pendulum on the slider bar to failure of the rubber specimen, is typically on the order of about 10 milliseconds. In accordance with the desired information to be recorded, tests may or may not be carried out until failure of the specimen. If the tensile impact force is less than the breaking force, the apparatus can be used to obtain dynamic stress-strain curves without break. In order to obtain reliable information on the tensile strength of the rubber sample, it is believed that at least 100 data points should be recorded during the experiment, thus requiring the collection of at least 10,000 data points per second. Therefore, the data acquisition system must be selected accordingly. Since there are two load cells and two displacement transducers, four channels are used for data acquisition, and the data acquisition device should be capable of recording at least 40,000 data per second/per channel.

Notably, because both ends of a rubber sample S are pulled apart in operation of apparatus 10, the middle of the sample effectively remains stationary. This is seen to be very advantageous because it allows for visual observation of the fracture phenomena. Particularly, high speed camera 70 is focused upon the middle of specimen S, and is programmed to visually capture what happens to specimen S during the test. The deformation and fracture processes under this invention typically take place within 10 milliseconds, so a camera with a shutter speed of at least 1 millisecond (1,000 frames per second) is believed sufficient to capture these events. Even faster shutter speeds are desirable, and even slower shutter speeds may be found to yield useful visual information.

Experimental Section

Further information regarding the present invention is provided hereinbelow. Particularly provided are experimental results relating to the use of the present invention.

1. Introduction

There are many situations in which tires may rupture under very high strain rates. Consider the example of an automobile tire with a radius $r_o=30.5$ cm that is traveling at a speed $V_o=89$ km/hr (see FIG. 1). The tire lug at point C will impact a 2.54 cm bump at approximately $$V_c = \frac{r_c V_o}{r_o} = 156 \text{ cm/s}.$$

If the tire lug of this vehicle were to have a depth $d=0.51$ cm, it would experience a shear strain rate $$\dot{\gamma} = \frac{V_c \sin\frac{\theta_c}{2}}{d} = 404 \text{ s}^{-1}.$$

Airplane and off-road vehicle tires may experience even higher strain rates upon landing or while driving over rough terrain. It is thus desirable to describe material response under such (and similar) conditions.

The objective of this study is to devise a simple experiment that can be used to obtain rate-dependent deformation and fracture characteristics of a rubber specimen (here SBR) under impact tensile loading. Such characteristics can help researchers identify deformation and fracture parameters that can be used to predict the impact failure of articles (e.g., tires) made of such rubber.

The most extensive data on the rate-sensitivity of the tensile deformation and fracture of rubber are those of B. A. Dogadkin and D. M. Sandromirski, "Effect of Temperature and the Rate of Stretching on the Tensile Strength of Vulcanizates", Rubber Chemistry and Technology, Vol. 25, 1952, pp. 50-55. These measurements were made on GR-S gum vulcanizates and only covered a range of strain rates of 0.04-0.32 s$^{-1}$. D. S. Villars, "Ultra Speed Tensile of Rubber and Synthetic Elastomers", J. Appl. Phys., Vol. 21, 1950, pp. 565-573, measured the tensile strength and breaking extension of dumbbell specimens of several gum and filled vulcanizates extended at strain rates between 1-10 s$^{-1}$. P. Kainradl, F. Handler, "Investigation on Notch Sensitivity of Vulcanisates", Kaut. Un Gummi, Vol. 12, No. 9, 1959, pp. 239-46, reported tensile strength measurements for several filled vulcanizates, obtained with dumbbell specimens extended at four different rates of extension ranging from $10^{-2}$-$10^3$ s$^{-1}$. H. W. Greensmith, "Rupture of Rubber: Effect of Rate of Extension in Tensile Tests", Journal of Applied Polymer Science, Vol. 3, No. 8, 1960, pp. 175-182, reported load extension data using ring specimens extended at various rates from $10^{-3}$-10 s$^{-1}$. All of these experimental studies indicate that tensile strength and breaking extension increase with the rate of extension of the specimen. Unfortunately, complete load extension curves are lacking in most of these papers, thus making it hard to develop a dynamic constitutive equation for rubber at high impact rates.

Herein, a new experimental technique is provided for large strain/high strain rate tensile testing of elastomers. Complete load-extension curves are given for SBR dumbbell specimens extended at impact rates ranging from $10^{-2}$-$10^{-3}$ s$^{-1}$. The following disclosure is divided into two parts: (a) the experimental setup and results and (b) the analysis and discussion of the results. The later part is a first step in establishing high stain-rate constitutive relations for SBR and other elastomers.

High strain-rate constitutive relationships for SBR and other elastomers are lacking to date. Most researchers employ the time-temperature superposition, i.e., M. L. Williams, R. F. Landel and J. D. Ferry, "The Temperature Dependence of Relaxation Mechanisms in Amorphous Polymers and Other Glass-Forming Liquids", J. Am. Chem. Soc., Vol. 77, 1955, pp. 3701-3707, to analyze high strain rate behavior, and some results produced by utilizing this theory can be found in T. L. Smith, "Dependence of the Ultimate Properties of GR-S Rubber on Strain Rate and Temperature", Journal of Polymer Science, Vol. 32, 1958, pp. 99-113. J. S. Bergström and M. C. Boyce, "Constitutive Modeling of the Large Strain Time-Dependent Behavior of Elastomers", J. Mec. Phys. Solids, Vol. 46, No 5, 1998, pp. 931-954, presented rate-dependent constitutive models for carbon black filled Chloroprene rubber subjected to time-dependent strain histories. The model was based on experimental results from an Instron servohydraulic uniaxial testing machine and the stain rates were less than 1 s$^{-1}$. Most recently, L. M. Yang, V. P. W. Shim, C. T. Lim, "A Visco-Hyperelastic Approach to Modeling the Constitutive Behavior of Rubber", International Journal of Impact Engineering, Vol. 24, 2000, pp. 545-560, proposed a visco-hyperelastic constitutive equation for rubber under high strain rate, but this equation was specifically developed for compression of a rubber pad, in which strains were less than 100%. Currently, no constitutive relationship for impact tensile behavior of rubber, whereby strains can reach up to 600%, has been proposed. Experimental results are presented herein with a focus toward developing such a constitutive model.

Materials and Experimental Setup

Rubber Specimen

Figure 6:
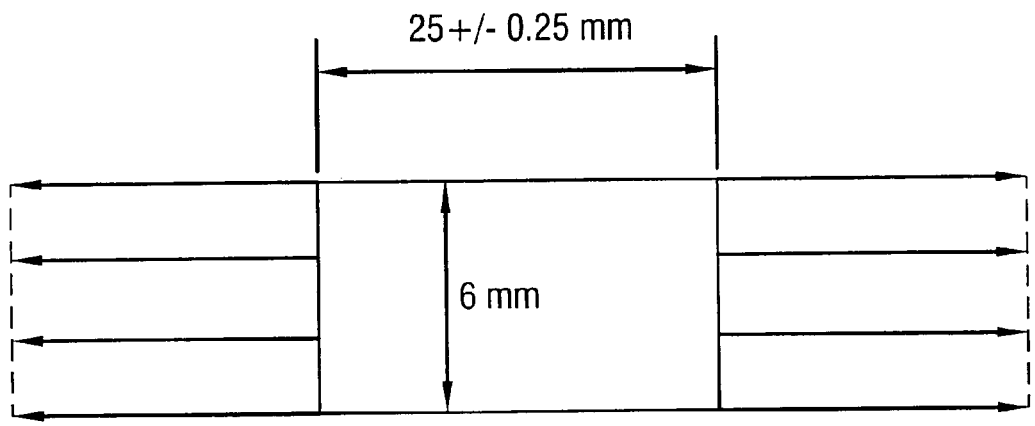
FIG. 6 is a diagram of the rubber specimens used in the Experimental section herein.

The impact tensile specimen that is used in the experiment is not the standard impact test piece but an ASTM standard D 412, ASTM D412, Annual Book of ASTM Standards, Vol. 09.01, 1998, pp. 43-55, Die C dumbbell specimen as shown in FIG. 6. The ends of the dumbbell are clamped by grips, and the solid line in FIG. 5 indicates the effective geometry of the specimen. The specimen is styrene-butadiene rubber (SBR), and the recipe for the specimen is given in Table 1.

TABLE 1

Recipe for SBR used in the tensile specimens.

| | SBR 1502 | ZnO | Sulfur | St. Acid | MBTS | TMDT |
|---|---|---|---|---|---|---|
| PHr | 100 | 5 | 2 | 2 | 1.6 | 0.4 |

Experimental Setup

A Charpy impact apparatus is used to achieve high strain rate behavior in the rubber. A Charpy apparatus that is designed for metals is used instead of one that is designed for polymers and elastomers for two reasons: (1) the pendulum height used for polymers is too low to provide high enough impact velocities and (2) the weight of the pendulum, which provides inertial forces, is not large enough to achieve a constant deformation rate throughout the experiment. In this experiment, the pendulum height is varied from about 2.5 inches to about 40 inches, and the pendulum weight is 30 lbs.

The experimental setup is shown in FIGS. 1(A) and (B) and FIGS. 2, 3, and 5, and has been discussed above. Circular motion of the pendulum is converted to a linear motion by striking one end of a slider bar, which moves in a groove. Two mechanical stops are added to the design: one is used to restrict the stroke length of the slider bar and the other is used to prevent the slider bar from rebounding if the rubber does not break. Friction between the slider bar and guides is minimized with a good lubricant. One end of the slider bar is attached to two identical copper cables, which are pulled instantly upon impact of the slider bar. Each cable is directed around a pulley and transfers linear motion to guided bases and grips that are attached to either ends of the rubber dumbbell specimen. Notably, in conventional high strain rate experiments only one grip moves while the other grip remains fixed, and, therefore, the center (in non-notched specimens) or the notch (in notched specimens) moves. With the apparatus of this invention, it is possible to observe crack propagation in the middle of the specimen, because the equal grip separation velocities on both sides of the specimen localize the middle of the specimen making it possible to visually record crack propagations with high-speed camera photography (generally represented in the FIG. 1A at 70).

The speed of the grips can be adjusted by varying the drop height of the pendulum. The maximum drop height of pendulum was 1.52 m, providing about 16.93 m/s of grip velocity. The stroke length of the slider bar controls the grip displacement. The present experiment was designed to give a maximum stroke length range of 0.41 m. The stroke length can be adjusted by simply repositioning the slider bar at the beginning of the experiment. The total grip displacement is twice as much as the stroke length of the bar since the motion of the slider bar is transferred equally to the two grips. Likewise, the grip velocity is twice that of the slider bar velocity.

The specimen is mounted on a rigidly supported test fixture. The grips are designed to be unconstrained, i.e. they move freely upon tensile impact loading. The only contact between the grips and the structure is through the load-cells, which are bolted to guided bases through plates, as shown and discussed in FIG. 5. The copper cables pull guided bases that slide freely along steel rails. The copper cables are connected to the guided bases by springs, which tend to smooth out the applied tensile load. When the copper cables suddenly pull the guided bases, the load cells hit the backside of the grips and the grips pull on the specimen. The tensile force is therefore measured as a compressive force on the backside of the rectangular slots in the grips. PCB 200-BO1 piezoelectric dynamic load cells with a range of 0-89 N are used to measure the tensile impact loads. RDP D5 Linear Variable Differential Transformers (LVDT Displacement transducers) with a range of ±150 mm are also attached to the guided bases to measure the grip separation distance.

The data acquisition device used in experiments herein was a DATAQ DI-720-USB. This data acquisition device has the ability to collect 300,000 data points per second per channel. An 8-Channel PCB 482A22 Signal Conditioner was used for the force sensors, and two RDP S7AC Transducer Amplifiers were used for the displacement transducers (LVDT's). The actual data acquisition was restricted by the storage speed of the data processor equipment. The speed used in this work was 100,000 data points per second. Since there were two load cells and two displacement transducers, four channels were used for data acquisition. Thus, each channel recorded 25,000 data points per second, which was sufficient for this type of application.

Results

Dynamic Stress-Strain Curves

Figure 7:
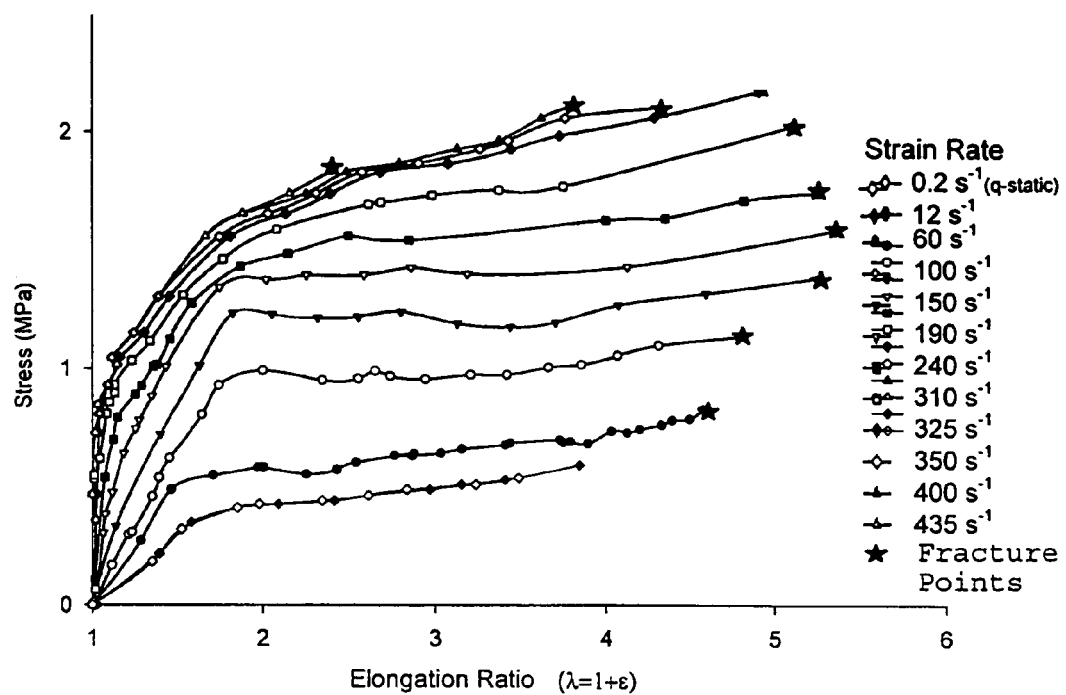
FIG. 7 provides stress-strain curves for styrene-butadiene rubber (SBR) tested in the Experimental section.

FIG. 7 shows the stress-strain curves for the SBR specimen under quasi-static and impact tensile loading. The star denotes the point at which fracture occurs. Each experiment was repeated 4-10 times to ensure repeatability of the data. Those tests for which the specimen did not break in the middle were discarded. The results from the acceptable tests were found to be within 10% of each other. The stress-strain curves, which are shown in FIG. 7, show plots of the median values for each test. The tensile strength and fracture strain (fracture points) were taken as average values. The quasi-static experiment (lowest curve) was done using an Instron universal testing machine.

Figure 8:
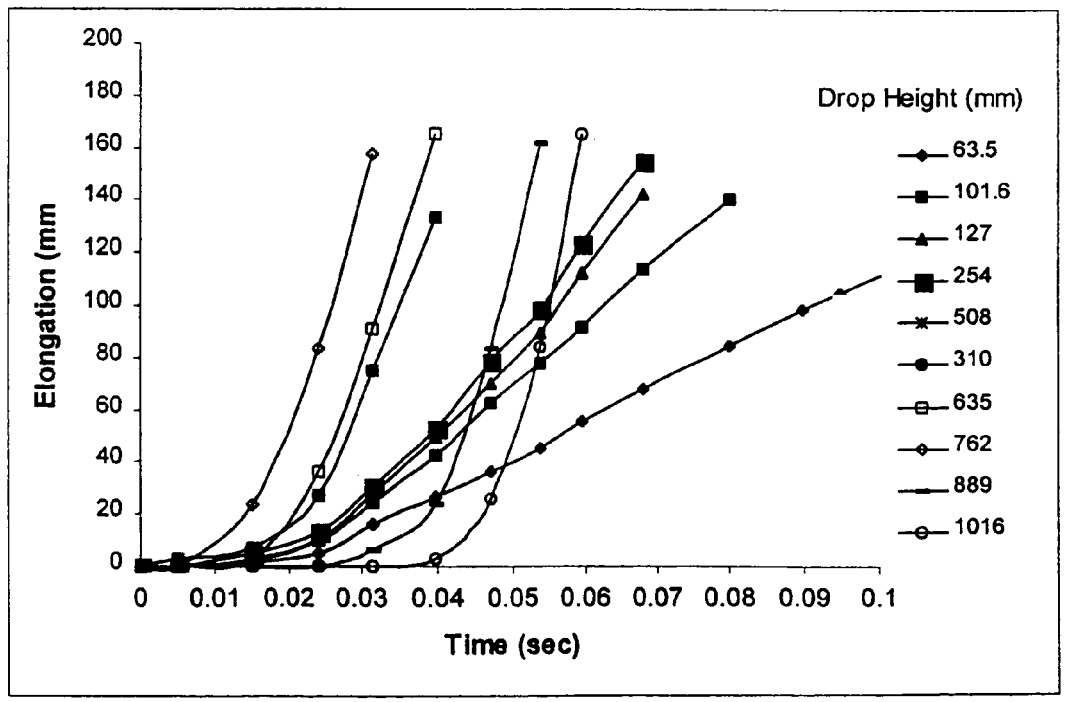
FIG. 8 provides elongation versus time graphs for SBR tested in the Experimental section.

The strain rate for each impact test was obtained from the plot of FIG. 8, which shows the variation of the elongation with time that is associated with each drop height. The strain rates during each experiment are approximated as the final slope of the elongation vs. time curve in FIG. 8. Table 2 summarizes the strain rate values that were calculated for each drop height.

TABLE 2

Strain rates associated with drop heights.

| Drop Height (mm) | 63.5 | 101.6 | 127 | 254 | 381 | 508 | 635 | 762 | 889 | 1016 |
|---|---|---|---|---|---|---|---|---|---|---|
| Strain Rate ($s^{-1}$) | 60 | 100 | 150 | 190 | 240 | 310 | 325 | 350 | 400 | 435 |

Rate-Dependent Behavior

The dynamic stress-strain curves reveal several types of deformation and fracture behavior as the strain rate increases:

1. Initial and final moduli can be calculated by constructing tangent lines on the stress-strain curves roughly between elongation ratios 1-2 and 2-6, respectively. A "knee" point is defined at the intersection of the two tangent lines. The "knee" signifies yielding in the rate-dependent stress-strain curves.

Figure 9:
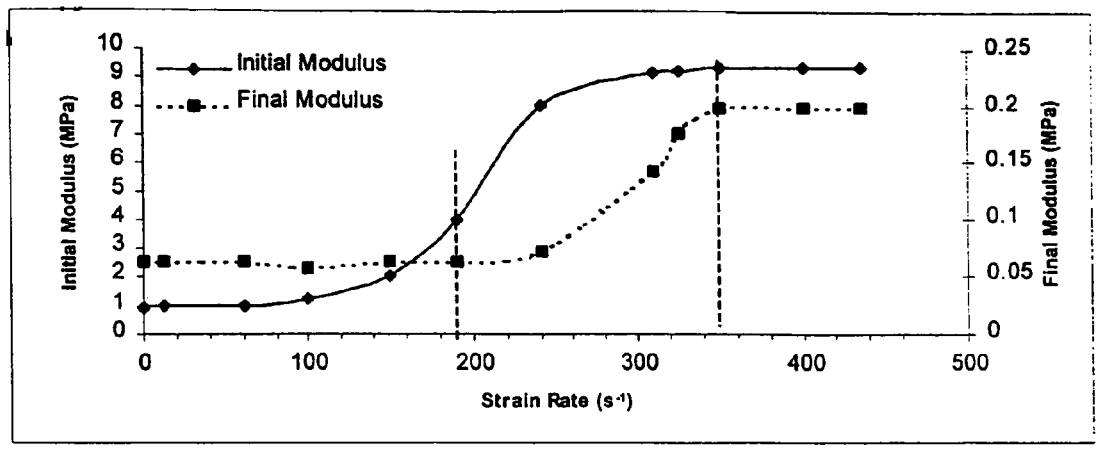
FIG. 9A provides initial and final moduli versus strain rate, FIG. 9B provides yield stress versus strain rate, and FIG. 9C provides tensile strength versus strain rate for SBR tested in the Experimental section.
Figure 9:
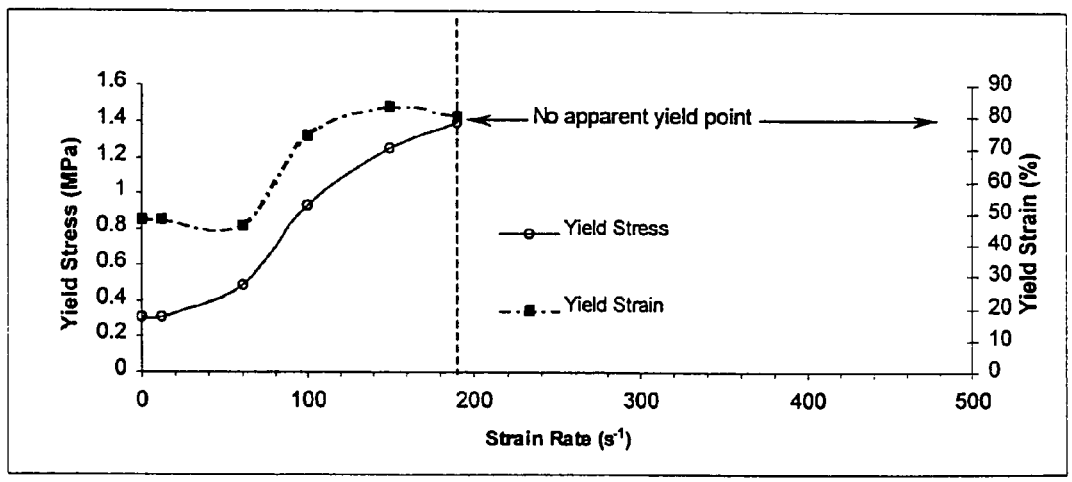
Figure 9:
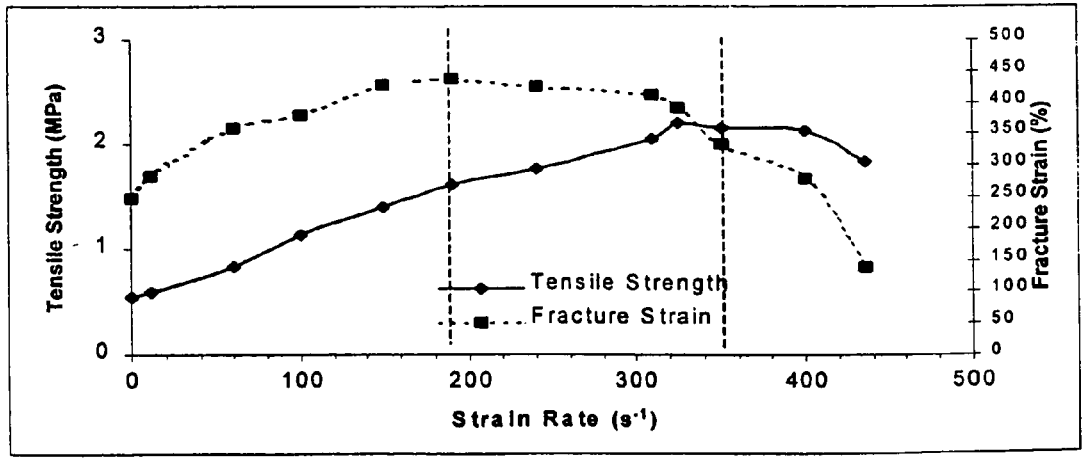

2. FIG. 9A shows that the initial and final moduli generally increase as the strain rate increases. However, the final modulus is roughly constant until a strain rate of 190 $s^{-1}$ (indicated by the first vertical dashed line in FIG. 9A). When the strain rate is greater than 190 $s^{-1}$ the final modulus increases more rapidly with increasing strain rate until a strain rate of 325 $s^{-1}$ (indicated by the second vertical dashed line in FIG. 9A). Beyond a strain rate of 325 $s^{-1}$, it becomes difficult to distinguish between an initial modulus and a final modulus and they do not vary much with increasing strain rate.

3. Both the yield stress and strain, which are indicated by the "knee," increase with increasing strain rate as shown in FIG. 9B until the strain rate reaches 190 s$^{-1}$. Beyond this strain rate, there is no apparent yield point.

4. FIG. 9C shows that the stress and strain at fracture both increase with increasing strain rate until the first critical strain rate at 190 s$^{-1}$. When the strain rates exceed 190 s$^{-1}$, the fracture stress increases while the fracture strain decreases for increasing strain rate. Thus, the maximum elongation ratio that the SBR can attain is 4.5. When the strain rates are greater than 325 s$^{-1}$, the fracture stress begins to decrease with increasing strain rates, while the strain at fracture is still decreasing with strain rate. Thus, the highest tensile stress that the SBR can attain is about 2.2 N/m$^2$.

Discussion of Results

Phases of Rate-Dependent Behavior

Figure 10:
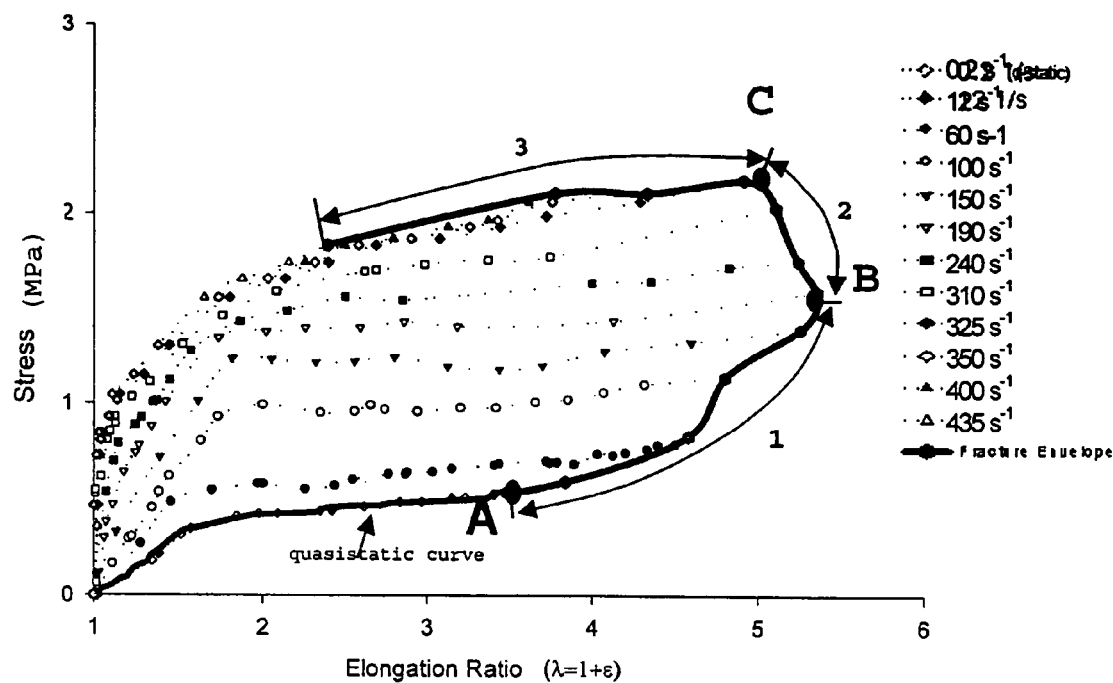
FIG. 10 provides stress versus elongation ratio data, and illustrates the phases of rate-dependent deformation and fracture behavior of SBR tested in the Experimental section.

The experimental results shown in FIGS. 9A-C suggest that there are three phases of rate-dependent deformation and fracture behavior in the SBR specimen. These phases are illustrated in FIG. 10. Phase 1 is bounded by points A and B, Phase 2 is bounded by points B and C, and Phase 3 is bounded by C and the origin. Point B distinguishes static behavior to the first (rate-sensitive) phase. Point C defines a transition point from the first phase to the second phase, when the fracture strain just begins to decrease with increasing strain rate. Point C marks the transition point from the second phase to a regime in which there is no distinction between initial and final moduli and all stress-strain curves appear to follow a master or limit curve. In Phase 1, the initial modulus, yield stress, tensile strength and fracture strain increase with increasing strain rate. In Phase 2, the final modulus and fracture stress increase and the fracture strain decreases as the strain rate increases. Finally, in Phase 3, only the fracture strain and stress decrease as the strain rate increases.

Figure 11:
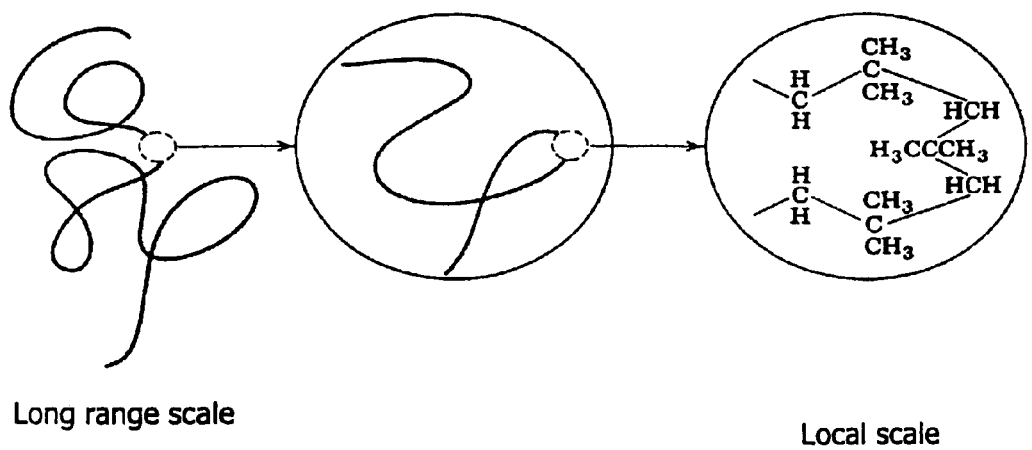
FIG. 11 diagrams the long-range and short-range contour relationships in SBR.

The occurrence of the above phases can be easily understood when one considers the composition and morphology of an elastomer such as SBR. The SBR specimen here is composed of long chain (linear) molecules of carbon-hydrogen monomers with occasional butadiene and styrene units. FIG. 11, which is taken from Ferry J. D., "Viscoelastic Properties of Polymers", Third Edition, John Wiley and Sons Inc., New York, 1987, shows three basic configurations or contour shapes of this flexible polymer molecule on spatial scales ranging from long-range (leftmost diagram) to short-range (rightmost diagram). Alfrey, T., "Mechanical Behavior of High Polymers", Interscience, New York, 1948, referred to these as convolutions, curls and kinks. The long chains intertwine to form entanglements (knots) and are cross-linked with sulphur. When under stress, molecules reptate (slide) except at the entanglements and cross-links. Relaxation, intermolecular slippage accompanied by some reversible breaking or swapping of bonds, also takes place during this time. The various types of slippage are distinguished by different relaxation times. Relaxation on a local scale involves relatively rapid de-orientation of the kinks in the molecular chains. Relaxation on a long-range scale involves very slow rearrangements of the convolutions with respect to each other. The relaxation time on the local scale is very short and the relaxation time on the long-range scale is long. In between these two ends of the spectrum, there is a wide and continuous range of spatial scales and relaxation times. As the loading rate increases, the amount of relaxation of the convolutions, curls and kinks vary and this accounts for rate-sensitivity of the modulus, tensile strength and fracture strain of the SBR specimen. Following this hypothesis, the following conclusions can be drawn for the above identified Phases 1-3:

Phase 1

The relaxation phenomenon is characterized by a loss of stress with time as a sample is held at constant strain. As the rate of strain is increased, the load duration becomes shorter. If the load duration is shorter than the relaxation time of some components in the SBR, they will not have time to relax. This gives a higher modulus or stress at a given elongation. The initial modulus, yield stress and tensile strength increase with increasing strain rate because they are associated with the relaxation times of the convolutions, but the final modulus is almost insensitive to strain rate because it is related to relaxation of the kinks in the SBR. Recall that kinks are associated with very short relaxation times, which fall within the load duration. Furthermore, the lack of relaxation causes less de-orientation of molecules and the strain at fracture becomes larger at high strain rate. At a strain rate of about 190 s$^{-1}$, the fracture strain starts to decrease with strain rate. At this point, the convolutions have stretched to a maximum extent. There is virtually no more relaxation associated with the convolutions. The knee in the stress-strain curve, which signifies "yielding," also becomes indistinguishable when the strain rate is greater than 190 s$^{-1}$ because there is no longer relaxation associated with convolutions.

Phase 2

Fracture behavior of SBR in this region is similar to that observed in impact tensile tests of a ductile material. In metals, the yield and tensile strengths increase while the fracture strain (ductility) decreases when the strain rate is increased. This is due to immobility or "lock-up" of dislocations, which do not have time to respond under very short load duration. The yield point signifies the onset of slip or dislocation motion, and the amount of dislocation motion or slipping that occurs determines the yield and tensile strengths. Any absence of slip therefore results in a higher yield and tensile strengths. Furthermore, dislocation motion accumulates to give a macroscopic strain. Thus the ductility is smaller when less slip occurs. Unlike metals, however, SBR samples return to their original lengths after fracture because they do not undergo permanent deformation.

In Phase 2, convolutions are experiencing "lock-up" when the strain rate increases beyond 190 s$^{-1}$. This in turn leads to a decrease in the fracture strain as the strain rate increases. However, the fact that the final modulus becomes rate-dependent in this region signifies that some relaxation on a local scale cannot take place during the loading time. As the rate of strain increases and the load duration decreases, there is less and less local scale relaxation and this contributes to an increase in the final modulus and tensile strength. When the strain rate of the SBR specimen is above 325 s$^{-1}$ there is very little change of the final modulus. It is at this point that there is no more relaxation on a local scale or on any scale for that matter.

Phase 3

Under very high deformation rates (Phase 3), relaxation, even on a very local scale, is severely restricted and the modulus remains insensitive to the rate of strain. The fracture strain decreases again because of locking that prevents slip. Variation of the tensile strength, however, appears to be caused by something else. The tensile strength could decrease as the strain rate increases in Phase 3 because of stress concentrations at the tips of microcracks within the SBR. These crack tips may have been blunted when slipping occurred under lower strain rates. Without slip or very local deformation, crack tips would remain sharp and the stress would be concentrated at the crack tip. Thus it would be easier for the SBR to tear at very high strain rates, and this would result in a decrease of tensile strength.

Time-Temperature Superposition and Glass Transition

In this section, time-temperature superposition theory is employed to estimate glass transition temperature. To superpose data measured at different temperatures on a time scale, a shift factor is determined by the following expression:

$$\ln a_T = \frac{C_1 \times (T - T_0)}{C_2 + T - T_0} \quad (1)$$

where $T_o$ is a reference temperature at which the data is to be shifted, $C_1$ and $C_2$ are material parameters, T is the test temperature and $a_T$ is the shift factor. Equation (1) is known as the Williams-Landel-Ferry (WLF) equation in the literature. For SBR, $C_1=-8.86$ and $C_2=101.6$, Ferry J. D., "Viscoelastic Properties of Polymers", Third Edition, John Wiley and Sons Inc., New York, 1987. The strain rate at the reference temperature is found by multiplying the strain rate at the test temperature by $a_T$.

The results of the present experiment suggest that glass transition occurs between points B and C in FIG. 10; the transition to the glassy state begins at point B and ends at point C. The SBR is in a glassy state during Phase 3. Let the reference temperature be equal to the temperature at the onset of glass transition in a quasi-static test, where the strain rate is assumed to be 0.2 $s^{-1}$. The shift factor to transform point B, i.e., a strain rate of 190 $s^{-1}$ at 297° K (room temperature), to a strain rate of 0.2 $s^{-1}$ at $T_0$, is calculated from the following expression:

$$190 a_T = 0.2 s^{-1} \quad (2)$$

The above equation gives $a_T=1.053\times 10^{-3}$. Using this shift factor in Eq. (1), one gets $T_0=245.56°$ K$\cong-27°$ C. as the temperature for the onset of glass transition. Similarly, the shift factor to transform point C, i.e., a strain rate of 325 $s^{-1}$ at 297° K, to a strain rate of 0.2 $s^{-1}$ at $T_0$, is calculated from the following expression:

$$325 a_T = 0.2 \ s^{-1} \quad (3)$$

Equation (3) gives $a_T=6.15\times 10^{-4}$ and using this shift factor in Eq. (1), one gets $T_0=207.54°$ K$\cong-65°$ C. as the temperature at the end of glass transition region.

The glass transition temperature should therefore be in the range of −65° C. to −27° C. This predicted range for the glass transition temperature appears to be reasonable since the glass transition temperature for SBR generally lies between −60° C. and −50° C., Ferry J. D., "Viscoelastic Properties of Polymers", Third Edition, John Wiley and Sons Inc., New York, 1987.

Dynamic Fracture Mechanics

Figure 12:
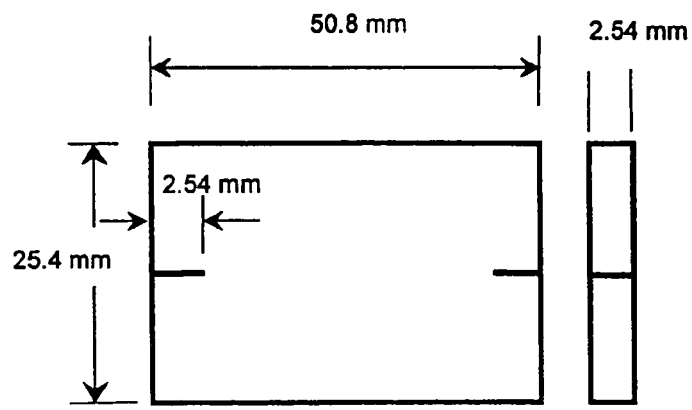
FIG. 12 is a diagram of the double-edge notched SBR specimens employed in the Experimental section.

The tensile impact apparatus was also used to investigate dynamic crack propagation in double-edge notched specimens shown in FIG. 12, with dimensions provided therein. These specimens were inserted between the grips of the apparatus 10, and the resulting force-extension curves were obtained for different strain rates. The double-edge notch configuration was chosen so the specimen was in uniaxial tension only (a single-edge notch configuration would produce combined tension and bending at the crack tip, and the present invention could certainly be used with such specimens). Unlike the uniaxial tests, strain and strain rate vary in the specimen, being largest at the crack tip.

Figure 13:
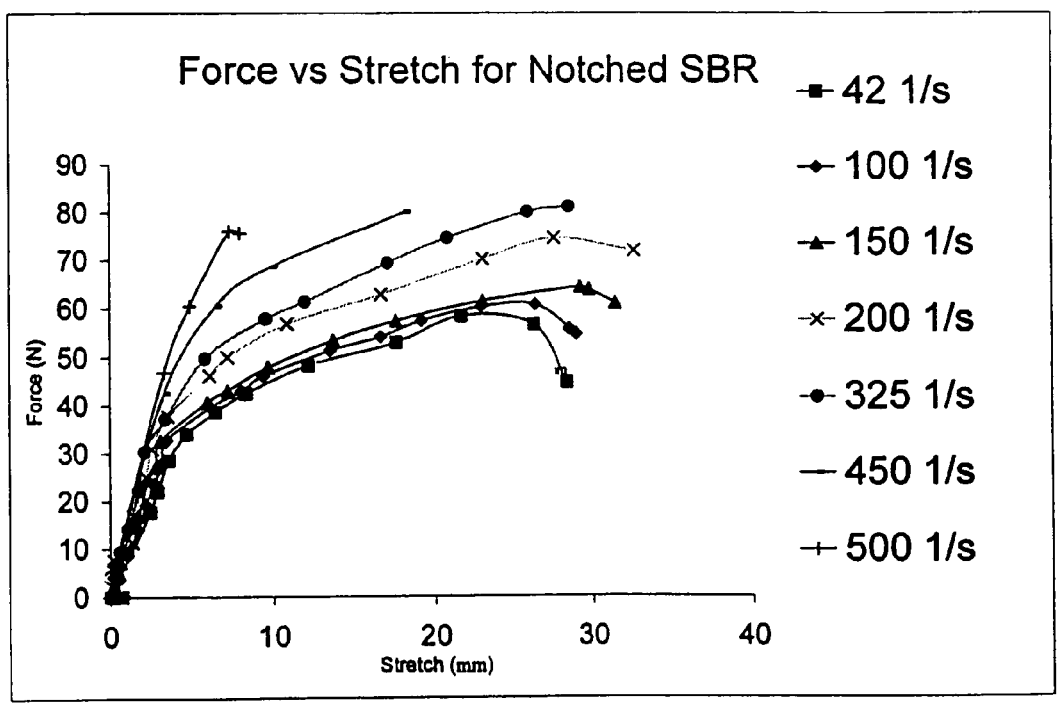
FIG. 13 provides force-extension curves for notched SBR samples as tested in the Experimental section.

The results, shown in FIG. 13, reveal that the fracture process, i.e., crack propagation at the crack tip, is very rate-dependent. At loading rates below 200 $s^{-1}$, there is localized necking before fracture; the crack tip blunts and the specimen elongates in the neck region before rapid crack propagation (fracture). Both the maximum force and deformation at fracture increase with the applied strain rate in this region. The work prior to fracture (area under the force-deformation curve) increases with increasing strain rate. At strain rates above 200 $s^{-1}$, the specimen stretches and breaks with no necking. The force at fracture remains roughly constant, but the deformation at fracture decreases with increasing strain rate. The work prior to fracture decreases with increasing strain rate. Thus, above strain rate of 200 $s^{-1}$ the rubber has a greater propensity to fracture with a pre-existing flaw.

The tensile impact apparatus could be used to characterize behavior at the crack tip using a high-speed camera. In the present experiments, the deformation and fracture processes take place within 10 milliseconds, so a camera with a shutter speed of at least 1 millisecond (1,000 frames per second) is believed sufficient to capture these events. Of course, even faster shutter speeds are desirable, and there is no upper limit on the desired number of frames per second for a camera that might be employed with the apparatus of this invention. Furthermore, rate-dependent hyperelastic or hyper-viscoelastic constitutive equations derived from dynamic stress-strain curves can be incorporated into finite element analysis in order to calculate fracture parameters, such as energy release rates, stresses or strains.

Conclusion

An experimental study was performed to characterize the tensile deformation and fracture behavior of SBR rubber under strain rates that reach up to 435 $s^{-1}$. A tensile impact experiment using the apparatus of this invention was designed to get the desired strain rates and impact tensile loading. Our experiments showed that the rate-dependence of the deformation and fracture characteristics of the elastomer occur differently in three phases:

1. The first phase occurs when the strain rate ranges from 1-190 $s^{-1}$. In this phase, the initial modulus, yield stress, tensile strength and fracture strain increase with increasing strain rate because the load duration becomes progressively shorter than the relaxation times of the convolutions. The final modulus is insensitive to strain rate because it is related to relaxation on a local scale.
2. The second phase occurs when the strain rate ranges from 190-325 $s^{-1}$. In the second phase, the initial modulus remains roughly constant while the final modulus increases with increasing strain rate. The stress at fracture continues to increase but the fracture strain decreases as the strain rate increases. A lack of stress relaxation on a local scale during the very short load duration is the reason for the increase in final modulus and tensile strength. The fracture strain decreases as the strain rate increases because slipping mechanisms are experiencing "lock-up."
3. The third or final phase occurs when the strain rate of the SBR is above 325 $s^{-1}$. Here there is no distinction between initial and final moduli and all stress-strain curves follow a master curve because there is virtually no stress relaxation taking place in the specimen. The tensile strength decreases with increasing strain rate because of stress concentrations at the tip of microcracks. These crack tips would have been blunted if the molecular chains in the SBR had time to slip.

The tensile impact apparatus was designed so that it could also be used to characterize behavior at the crack tip using a high-speed camera. Preliminary results on dynamic crack propagation in double-edge notched SBR panels revealed that the fracture process is very rate-dependent. Below a critical strain rate, fracture was preceded by crack tip blunting and localized necking of the entire specimen. Both the maximum force and deformation at fracture increased with the applied strain rate so that the work prior to fracture (area under the force-extension curve) increased with increasing strain rate. Above the critical strain rate, the specimen stretched and broke with no necking. The force at fracture remained roughly constant, but the deformation at fracture decreased with increasing strain rate so that the work prior to fracture decreased with increasing strain rate. Thus rate-dependency and phase transformation are very important features in the dynamic fracture toughness of SBR.

In light of the foregoing, it should thus be evident that the process of the present invention, providing a tensile impact apparatus, substantially improves the art. While, in accordance with the patent statutes, only the preferred embodiments of the present invention have been described in detail hereinabove, the present invention is not to be limited thereto or thereby.

What is claimed is:

1. A tensile impact apparatus comprising:
   a slider bar having an impact surface and capable of sliding on a support member;
   a first guided base retained on a support rail and capable of linear movement thereon, said first guided base communicating with a first grip through a first load cell;
   a second guided base retained on a support rail and capable of linear movement thereon, said second guided base communicating with a second grip through a second load cell, said first and second grips being substantially aligned for linear movement towards or away from each other and further being adapted for gripping opposed ends of a rubber sample;
   a first cable connected between said slider bar and said first guided base;
   a second cable connected between said slider bar and said first guided base;
   a first displacement transducer associated with said first guided base;
   a second displacement transducer associated with said second guided base; and
   a pendulum adapted for striking said slider bar such that, when said pendulum strikes said slider bar, said slider bar slides on its associated support member and pulls said first and second cables such that said first and second guided bases are substantially simultaneously moved away from each other by the pulling force of their respective first and second cables, and said first and second grips are also substantially simultaneously moved away from each other due to their respective communication with said first and second bases through said first and second load cells.

2. The tensile impact apparatus of claim 1, further comprising a camera capable of recording the crack tip fracture of a rubber sample when a rubber sample is gripped between said first and second grips and stretched by movement of said guided base.

3. A process for strain rate testing a rubber sample under tensile impact loading comprising the steps of:
   securing a rubber sample at opposed ends thereof; and
   moving the opposed ends away from each other substantially simultaneously and at substantially identical velocities such that the middle of the rubber sample remains substantially stationary, while the movement of the opposed ends stretches the rubber sample at impact rates
   wherein the method permits the determination of a stress-strain curve up to break at a strain rate of at least $10\ s^{-1}$ for the rubber sample.

4. The process of claim 3, further comprising visually recording the physical affect of said step of moving on the middle section.

5. A method for testing a rubber sample under impact loading comprising:
   (i) providing a rubber sample;
   (ii) providing a tensile impact apparatus that comprises:
      a slider bar having an impact surface and capable of sliding on a support member,
      a first guided base retained on a support rail and capable of linear movement thereon, the first guided base communicating with a first grip through a first load cell,
      a second guided base retained on a support rail and capable of linear movement thereon, the second guided base communicating with a second grip through a second load cell, the first and second grips being substantially aligned for linear movement away from each other and further being adapted for gripping opposed ends of a rubber sample,
      a first cable connected between the slider bar and the first guided base,
      a second cable connected between the slider bar and the first guided base,
      a first displacement transducer associated with the first guided base,
      a second displacement transducer associated with the second guided base, and
      a pendulum adapted for striking the slider bar such that, when the pendulum strikes the slider bar, the slider bar slides on its associated support member and pulls the first and second cables such that the first and second guided bases are substantially simultaneously moved away from each other by the pulling force of their respective first and second cables, and the first and second grips are also substantially simultaneously moved away from each other due to their respective communication with the first and second bases through the first and second load cells; and
   (iii) determining a stress-strain curve at a constant strain rate for the rubber sample.

6. The method of claim 5, further comprising visually recording the crack tip fracture of the rubber sample when the rubber sample is placed between the first and second grips and stretched by movement of the guided base.

* * * * *

UNITED STATES PATENT AND TRADEMARK OFFICE
CERTIFICATE OF CORRECTION

PATENT NO. : 7,320,242 B2 Page 1 of 1
APPLICATION NO. : 10/387095
DATED : January 22, 2008
INVENTOR(S) : Michelle S. Hoo Fatt et al.

It is certified that error appears in the above-identified patent and that said Letters Patent is hereby corrected as shown below:

Title Page; item (75);
The third inventor's name should be --Joseph Padovan--

Signed and Sealed this

Twenty-ninth Day of April, 2008

JON W. DUDAS
*Director of the United States Patent and Trademark Office*